(12) United States Patent
Kalchauer et al.

(10) Patent No.: US 6,465,674 B1
(45) Date of Patent: Oct. 15, 2002

(54) DUST RECIRCULATION IN THE DIRECT SYNTHESIS OF CHLOROSILANES AND METHYLCHLOROSILANES IN A FLUIDIZED BED

(75) Inventors: Wilfried Kalchauer, Burghausen (DE); Herbert Straussberger, Mehring-Oed (DE); Willi Streckel, Mehring-Oed (DE); Jochen Gross, Mehring-Oed (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/119,626

(22) Filed: Apr. 10, 2002

(30) Foreign Application Priority Data

Apr. 12, 2001 (DE) .......................... 101 18 483

(51) Int. Cl.$^7$ ................................. C07F 7/16
(52) U.S. Cl. ...................................... 556/472
(58) Field of Search ............................. 555/472

(56) References Cited

U.S. PATENT DOCUMENTS 4,281,149 A  7/1981  Shade
4,328,353 A  5/1982  Shah
5,625,088 A  4/1997  Kalchauer

FOREIGN PATENT DOCUMENTS

| EP | 0 201 200 | 11/1986 |
| EP | 0 784 057 | 7/1997 |
| EP | 0 900 802 A2 | 3/1999 |
| EP | 0 900 802 | 3/1999 |

*Primary Examiner*—Paul F. Shaver
(74) *Attorney, Agent, or Firm*—Brooks & Kushman P.C.

(57) ABSTRACT

A continuous process for the direct synthesis of silanes of the formula 1

$$R_aSiCl_{4-a} \qquad (1)$$

involves reacting finely divided silicon metal with R—Cl in a fluidized bed, where
R is hydrogen, methyl or ethyl and
a is 0, 1, 2, 3 or 4, where a product stream comprising gaseous silanes of the formula 1, further gaseous reaction products, unreacted RCl and silicon-containing dust is discharged from the fluidized bed, wherein at least part of the dust is introduced in the form of a suspension in a liquid selected from among liquid silanes of the formula 1, further liquid reaction products and mixtures thereof, into the fluidized bed.

7 Claims, No Drawings

DUST RECIRCULATION IN THE DIRECT SYNTHESIS OF CHLOROSILANES AND METHYLCHLOROSILANES IN A FLUIDIZED BED

BACKGROUND OF THE INVENTION

1. Field of the Invention

The invention relates to a process for the direct synthesis of chlorosilanes and methylchlorosilanes in a fluidized bed, in which process silicon-containing dust formed is introduced in the form of a suspension in a liquid into the fluidized bed.

2. Background Art

In the Müller-Rochow direct synthesis, chloromethane is reacted with silicon in the presence of a copper catalyst and suitable promoters to produce methylchlorosilanes. In this process, very high selectivity to the target product dimethyldichlorosilane is necessary. Dimethyldichlorosilane is required, for example, for the preparation of linear polysiloxanes.

In the direct synthesis of chlorosilanes, silicon is reacted with hydrogen chloride, in the presence or absence of a copper catalyst, to form trichlorosilane and tetrachlorosilane. Chlorosilanes are required, for example, for the preparation of pyrogenic silica. Pyrogenic silicas can also be prepared from methylchlorosilanes and mixtures of methylchlorosilanes and chlorosilanes without the product quality being impaired.

In both processes, not only a very high productivity, measured as the amount of silanes formed per unit time and per reaction volume, but also a very high silicon conversion combined with reliable and flexible operation of the overall plant are required.

Both processes can be carried out batchwise, continuously or semicontinuously. In industrial production, they are preferably carried out continuously.

The continuous direct synthesis is carried out in fluidized-bed reactors in which chloromethane or hydrogen chloride and gaseous reaction products act as the fluidizing medium. The silicon required is milled to a powder having a particular particle size before the synthesis.

In the methylchlorosilane synthesis, the silicon powder is mixed with copper catalysts and promoters to form a catalyst-containing composition. This catalyst-containing composition is subsequently introduced into the fluidized-bed reactor and reacted therein. Unreacted chloromethane, gaseous methylchlorosilanes, gaseous by-products, catalyst constituents, and finely divided dusts leave the reactor.

In U.S. Pat. No. 4,281,149, FIG. 1 shows a system comprising a reactor, a main cyclone with recirculation and an after-cyclone with a dust collection vessel. In this process, part of the particulate material precipitated in the after-cyclone are subjected to a surface treatment and subsequently fed back into the reactor as solids. This is said to achieve a high silicon conversion. The gas stream leaving the cyclone(s) always still contains residual dust which has to be separated prior to the distillation of the methylchlorosilanes. U.S. Pat. No. 4,328,353 proposes that the gas stream which has passed through the cyclone be subjected to a hot gas filtration and the pulverulent material obtained here be recirculated to the reactor or discharged from the process. The possibility of passing these fine dusts without further treatment to a reaction with HCl (chlorosilane synthesis) is also disclosed. EP-A-900802 likewise describes a hot gas filtration with subsequent recirculation of the particles.

When very fine dusts are introduced directly into fluidized-bed reactors of the chlorosilane synthesis or methylchlorosilane synthesis, these particles are very quickly swept out again, and are thus not available to the reaction. At the same time, the recirculation of fine dusts in this manner leads to a considerably greater load on the entire dust precipitation system.

Furthermore, these very fine silicon dusts in dry form are extremely reactive toward air and atmospheric moisture, i.e. when this product stream accidentally comes into contact with air, as may occur in the case of a malfunction in the plant, spontaneous ignition has to be reckoned with.

SUMMARY OF THE INVENTION

It is an object of the present invention to provide a continuous process for the direct synthesis of chlorosilanes and methylchlorosilanes in a fluidized bed, in which process the finely divided dusts which are formed and are entrained within the reaction product can be reused effectively.

DETAILED DESCRIPTION OF THE PREFERRED EMBODIMENT(S)

The invention provides a continuous process for the direct synthesis of silanes of the formula 1

$$R_a SiCl_{4-a} \qquad (1)$$

by reacting finely divided silicon metal with R—Cl in a fluidized bed, where
R is hydrogen, methyl or ethyl and
a is 0, 1, 2, 3 or 4,
where a product stream comprising gaseous silanes of the formula 1, further gaseous reaction products, unreacted RCl and silicon-containing dust is discharged from the fluidized bed, wherein at least part of the dust is introduced in the form of a suspension in a liquid selected from among liquid silanes of the formula 1, further liquid reaction products and mixtures thereof into the fluidized bed.

It has been found that the very fine dust particles formed in the continuous fluidized-bed process very readily agglomerate to form larger units or deposit on existing Si grains when the dust particles are introduced in the form of a suspension into a running fluidized-bed reactor. As a result, the silicon-containing dust remains in the fluidized bed for a prolonged period and is reacted effectively therein. An increased load on the dust precipitation system is thusly avoided. Even very fine silicon-containing dusts can be handled safely in the process, and a high overall silicon conversion is achieved. Disadvantages such as decreases in selectivity and/or reactivity and/or shortening of the operating time ("campaign") of the reactor in the methylchlorosilane synthesis can be avoided by this method.

The silicon required for the direct synthesis is milled to a powder having a particle size of preferably not more than 2000 μm, in particular not more than 500 μm, prior to the synthesis. The particle size of the recovered dust is preferably not more than 200 μm, in particular not more than 30 μm.

Further gaseous reaction products present in the product stream are mainly oligosilanes, carbosilanes, siloxanes and high-boiling cracking products. The gaseous reaction products are liquefied and, like the liquid silanes of the formula 1, may serve as suspension medium for the dust.

The term "suspension" refers to all mixtures of dust and liquid which are pumpable, including slurries and suspensions in which the dust particles remain suspended for only a short time after stirring in the dust. The suspensions are preferably capable of being sprayed, and are most preferably sprayed into the fluidized bed. To stabilize the suspensions, it is possible to add customary suspension aids. The suspension preferably contains from 0.5% by weight to 30% by weight, more preferably from 1% by weight to 10% by weight, of dust.

In the methylchlorosilane synthesis by the Müller-Rochow method, the silicon powder is mixed with copper catalysts and promoters to form a catalyst-containing composition. This catalyst-containing composition is subsequently introduced into the fluidized-bed reactor and reacted at a temperature of preferably 260–350° C. Since the reaction is exothermic, the heat of reaction which is liberated has to be removed by means of a cooling system. Gaseous products and finely divided dusts leave the reactor. Depending on the plant construction, it is possible, for example, for the relatively coarse entrained particles to be separated from the gas stream by means of one or more cyclones and be returned to the reactor or discharged from the system via dust collection vessels. The very fine entrained particles can be separated off in downstream components of the plant. In this way, a high conversion of silicon can be ensured.

The chlorosilane synthesis is carried out at a temperature of about 300–800° C.; the reaction is likewise exothermic but does not have to be catalyzed. The quality demands made of the silicon to be used are considerably less severe than in the methylchlorosilane synthesis, since in this case various elements present in the silicon as secondary components, for example Ni or Cr, do not act as catalyst poisons, and various silicide phases, for example $FeSi_2$, are able to react with HCl, unlike the case of MeCl.

It is possible for the dust collected in a chlorosilane synthesis to be introduced in the form of a suspension into the fluidized bed of a methylchlorosilane synthesis by the Müller-Rochow method, or for the dust collected in a methylchlorosilane synthesis by the Müller-Rochow method to be introduced in the form of a suspension into the fluidized bed of a chlorosilane synthesis.

Complete recirculation of all dusts into the fluidized-bed reactor as described, for example, in EP-A-900802, can cause catalyst poisons such as lead, chromium and nickel and unreactive particles such as iron suicides and slag to accumulate in the reaction system, particularly in the methylchlorosilane synthesis. As a result, the selectivity, reactivity and the operating time of the reactor can be reduced as a result. For this reason, preference is given to recirculating only from 10 to 90% by weight, in particular from 20 to 80% by weight, of the dust into the fluidized bed. In a further preferred variant, the recirculation of the dust, i.e. the introduction of the dust as a suspension into the fluidized bed, is carried out in phases, particularly at times at which an increased amount of fine dusts is obtained, as may be the case, for example, when starting up a reactor.

Solid/liquid separation by means of evaporation processes or filtration is more effective than solid/gas separation by means of hot gas filtration. Condensation of the product stream after hot gas filtration and/or distillation of the methylchlorosilanes therefore produces an additional liquid dust-containing methylchlorosilane product stream. This dust-containing methylchlorosilane product stream is preferably introduced as a suspension into the fluidized bed.

In the present process, equipment used for preparing methylchlorosilanes in a fluidized-bed reactor are preferably either (A) at least 2 cyclones, a subsequent condensation unit and a downstream concentrator unit or (B) at least 2 cyclones with subsequent hot gas filtration and a downstream suspension unit.

A preferred embodiment of the process is carried out using the equipment described in (A) above. The product stream leaving the fluidized-bed reactor of the methylchlorosilane synthesis passes through a 1st cyclone, where the relatively coarse particles are precipitated and recirculated to the reactor. In the 2nd cyclone, the finer particles are precipitated. These finer particles may either be returned in the form of a suspension to the reactor or may be discharged. Discharge can be carried out continuously or at intervals. At least part of the methylchlorosilanes formed are condensed from the remaining product stream by means of appropriate measures. Condensation can be achieved, for example, by passing the product stream into liquid methylchlorosilanes, by introducing this stream into a scrubbing tower operated using liquid methylchlorosilanes, or into a fractionation column provided with appropriate internals. After this process, the gaseous phase comprises mainly unreacted chloromethane and volatile methylchlorosilanes. The chloromethane is, after appropriate work-up, fed back into the production process. The liquid phase comprises mainly methylchlorosilanes and solids. The solids are concentrated by an appropriate method, for example filtration, in particular crossflow filtration, or evaporation of part of the methylchlorosilane, to such an extent that the suspension remains.

The solids-free methylchlorosilanes are passed to distillation while the suspension is sprayed into a running fluidized-bed reactor for preparing methylchlorosilanes and/or chlorosilanes.

When the suspension is sprayed into the reactor, the methylchlorosilanes vaporize and the dust particles agglomerate to form larger, quite stable aggregates, or may form stable deposits on existing Si grains. The size of the agglomerates depends very strongly on the chosen process conditions, for example the solids content of the suspension. Depending on size, the agglomerates remain in the reactor or are precipitated in the 1st cyclone and returned to the reactor. This portion of the agglomerates is thus once again available to the desired reaction. The smaller agglomerates are precipitated in the 2nd cyclone and leave the reaction system via this route. The methylchlorosilanes sprayed in ultimately end up in the distillation unit and do not have to be disposed of with the dust.

If the suspension is introduced into a reactor for preparing methylchlorosilanes, the activating effect of the catalyst-containing silicon particles which are already passing through a direct synthesis for preparing methylchlorosilanes, as described in U.S. Pat. No. 5,625,088, can simultaneously be achieved.

If the suspension is introduced into a reactor for preparing chlorosilanes and the liquid phase comprises mainly methylchlorodisilanes, part of the latter can be cleaved in the reactor to produce more useful methylchlorosilanes.

A further preferred embodiment of the process is carried out in the equipment described in (B) above. The product stream leaving the fluidized-bed reactor of the methylchlorosilane synthesis passes through the 1st cyclone. The coarser particles are precipitated there and returned to the reactor. The exit system is subjected to a hot gas filtration as described, for example, in U.S. Pat. No. 4,328.353. The dusts precipitated by this phase of the process are mixed with liquid methylchlorosilanes and/or methylchlorodisilanes or methylchlorosilanes laden with solids, which are obtained in the subsequent distillation section, so as to form a suitable suspension.

The suspension is preferably processed further as in embodiment (A) and, in particular, is introduced into a reactor for preparing chlorosilanes in order to prevent accumulation of interfering elements/compounds.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. In a continuous process for the direct synthesis of silanes of the formula 1

$$R_aSiCl_{4-a} \tag{1}$$

by reacting finely divided silicon metal with R—Cl in a fluidized bed, where

R is hydrogen, methyl or ethyl and a is 0, 1, 2, 3 or 4, where a product stream comprising gaseous silanes of the formula 1, further gaseous reaction products, unreacted RCl and silicon-containing dust is discharged from the fluidized bed, the improvement comprising introducing at least a portion of the dust in the form of a suspension in a liquid selected from among liquid silanes of the formula 1, further liquid reaction products and mixtures thereof, into the fluidized bed or into a fluidized bed of another process for direct synthesis of silanes.

2. The process of claim 1, wherein the suspension contains from 0.5% by weight to 30% by weight of dust.

3. The process of claim 1, wherein from 10 to 90% by weight of the dust is introduced into the fluidized bed in said suspension.

4. The process of claim 1, wherein the amount of dust introduced in the form of a suspension into the fluidized bed is varied with respect to time.

5. The process of claim 1, wherein the dust is introduced in the form of a suspension into the fluidized bed of a methylchlorosilane synthesis by the Müller-Rochow method.

6. The process of claim 1, wherein the dust is introduced in the form of a suspension into the fluidized bed of a chlorosilane synthesis.

7. The process of claim 1 further comprising separating larger silicon-containing particles in a first cyclone and reintroducing said larger silicon-containing particles back into the fluidized bed, and separating fine silicon-containing dust by means of a second cyclone or a hot gas filtration apparatus, and introducing said fine silicon-containing dust in the form of a suspension in a liquid into said fluidized bed.

* * * * *